United States Patent
Fujita et al.

(10) Patent No.: US 10,813,914 B2
(45) Date of Patent: Oct. 27, 2020

(54) COMPOSITION FOR CONTROLLING MICROSPORIDIA IN FISHES AND METHOD FOR CONTROLLING MICROSPORIDIA IN FISHES USING SAME

(71) Applicants: MARUHA NICHIRO CORPORATION, Tokyo (JP); THE UNIVERSITY OF TOKYO, Tokyo (JP)

(72) Inventors: Yukitoki Fujita, Yamaguchi (JP); Hiroshi Yokoyama, Tokyo (JP); Hiroki Ogawa, Tokyo (JP)

(73) Assignees: MARUHA NICHIRO CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/089,226

(22) PCT Filed: Mar. 30, 2017

(86) PCT No.: PCT/JP2017/013489
§ 371 (c)(1),
(2) Date: Sep. 27, 2018

(87) PCT Pub. No.: WO2017/170970
PCT Pub. Date: Oct. 5, 2017

(65) Prior Publication Data
US 2019/0111027 A1    Apr. 18, 2019

(30) Foreign Application Priority Data

Mar. 31, 2016 (JP) ................ 2016-070840
Mar. 13, 2017 (JP) ................ 2017-047531

(51) Int. Cl.

| | | |
|---|---|---|
| A61K 31/4184 | (2006.01) | |
| A61K 31/427 | (2006.01) | |
| A61K 31/27 | (2006.01) | |
| A01N 47/18 | (2006.01) | |
| A01N 43/52 | (2006.01) | |
| A61P 33/00 | (2006.01) | |
| A23L 33/00 | (2016.01) | |
| A61K 9/00 | (2006.01) | |

(52) U.S. Cl.
CPC .......... *A61K 31/4184* (2013.01); *A01N 43/52* (2013.01); *A01N 47/18* (2013.01); *A23L 33/00* (2016.08); *A61K 31/27* (2013.01); *A61K 31/427* (2013.01); *A61P 33/00* (2018.01); *A61K 9/0019* (2013.01); *A61K 9/0053* (2013.01); *Y02A 50/492* (2018.01)

(58) Field of Classification Search
CPC .......................... A61K 31/4184; A61P 33/00
See application file for complete search history.

(56) References Cited

U.S. PATENT DOCUMENTS

2004/0044055 A1    3/2004    Lieb et al.

FOREIGN PATENT DOCUMENTS

| CN | 1479725 A | 3/2004 |
|---|---|---|
| CN | 101536983 A | 9/2009 |
| CN | 102274174 A | 12/2011 |
| CN | 103037866 A | 4/2013 |

(Continued)

OTHER PUBLICATIONS

Athanassopoulou et al. In: Rogers C. (ed.), Basurco B. (ed.). The use of veterinary drugs and vaccines in Mediterranean aquaculture. Zaragoza: CIHEAM, 2009. p. 65-83 (Options Méditerranéennes-:Série A. Séminaires Méditerranéens; n . 86 (Year: 2009).*

(Continued)

*Primary Examiner* — James D. Anderson
(74) *Attorney, Agent, or Firm* — Foley & Lardner LLP

(57) ABSTRACT

A composition for controlling or preventing microsporidia in a fish or a seafood is prepared by using, as an active ingredient, at least one compound selected from the group consisting of compounds represented by the following chemical formula (I):

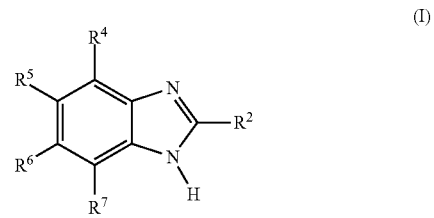

(wherein, $R^2$, $R^4$, $R^5$, $R^6$ and $R^7$ each independently represent a specific substituent), pharmaceutically acceptable salts thereof, and compounds generating the compounds represented by the chemical formula (I) by metabolism in the body of the fish or the seafood. By using this composition for controlling or preventing microsporidia in a fish to or a seafood, a method for controlling or preventing microsporidia in a fish or a seafood is provided, which prevents microsporidian infection in the muscle or organs of the fish or the seafood, and/or suppresses the growth of microsporidia in the muscle or organs of the fish or the seafood, and/or highly effective in eliminating microsporidia from the body of the fish or the seafood and also excellent in safety.

6 Claims, No Drawings
Specification includes a Sequence Listing.

(56) References Cited

FOREIGN PATENT DOCUMENTS

| JP | 57-106621 A | 7/1982 |
|---|---|---|
| JP | S57-106621 A | 7/1982 |
| JP | 2002-220309 A | 8/2002 |
| JP | 2004-511471 A | 4/2004 |

OTHER PUBLICATIONS

Athanassopoulou, et al., "An overview of the treatments for parasitic disease in Mediterranean aquaculture," *Options Mediterraneennes*, No. 86, pp. 65-83 (2009).

Didier et al., "Screening of compounds for antimicrosporidial activity in vitro," *Folia Parasitologica*, vol. 45, pp. 129-139 (1998).

Franssen, et al., "Susceptibility of *Encephalitozoon cuniculi* to Several Drugs In Vitro," *Antimicrobial Agents and Chemotherapy*, pp. 1265-1268 (Jun. 1995).

Gross, Treatment of Microsporidiosis including Albendazole, *Parasitol Res.*, vol. 90, pp. S14-S18 (2003).

Kano et al., "Studies on Pleistophora Infection in Eel, *Anguilla japonica*—II. Preliminary Tests for Application of Fumagillin," *Fish Pathology*, vol. 17, No. 2, pp. 107-114 (1982).

Katiyar et al., "In Vitro Susceptibilities of the AIDS-Associated Microsporidian *Encephalitozoon intestinalis* to Albendazole, Its Sulfoxide Metabolite, and 12 Additional Benzimidazole Derivatives," *Antimicrobial Agents and Chemotherapy*, pp. 2729-2732 (Dec. 1997).

Lallo et al., "Effect of Three Drugs against *Encephalitozoon cunicali* Infection in Immunosuppressed Miche," *Antimicrobial Agents and Chemotherapy*, vol. 57, No. 7, pp. 3067-3071 (Jul. 2013).

Saleh et al., "Development of a novel in vitro method for drug development for fish; application to test efficacy of antimicrosporidian compounds," *Veterinary Record*, 6 pages (Dec. 2014).

Schmahl, et al., "Treatment of Fish Parasites. 11. Effects of Different Benzimidazole Derivatives (albendazole, mebendazole, fenbendazole) on *Glugea anomala*, Moniez, 1387 (Microsporidial): Ultrastructural Aspects and Efficacy Studies," *Parasitol Res.*, vol. 84, pp. 41-49 (1998).

Silveira, et al., "In vitro cultivation of human microsporidium *Vittaforma corneae:* development and effect of albendazole," *Folia Parasitologica*, vol. 42, pp. 241-250 (1995).

Speare et al., "A Preliminary Investigation of Alternatives to Fumagillin for the Treatment of *Loma salmonae* Infection in Rainbow Trout." *J. Comp. Path.*, vol. 121, pp. 241-248 (1999).

Fish Disease Research (Japanese Society of Fish Pathology), vol. 11 (1976-1977), 180 pages (2015).

Takahashi et al., "Studies on Glugeosis of "Ayu"—II: Review of the Control Method (1), Effect of Fumagillin Oral Administration", Fish Disease Research (Japanese Society of Fish Pathology), vol. 11 (1976-1977), No. 2, pp. 83-88.

Notice of Reasons for Refusal issued in co-pending Japanese Patent Application No. 2017-047531, dated Nov. 8, 2017.

Takahashi, S. et al. "Studies on *Glugea* Infection of the Ayu, *Plecoglossus altivelis*—II. On the Prevention and Treatment—Fumagillin Efficacy as a Treatment", 1976, 6 pgs.

Kano, T. et al. "Studies on *Pleistophora* Infection in Eel, *Anguilla japonica*—II. Preliminary Tests for Application of Fumagillin", Fish Pathology, vol. 17(2), 1982, pp. 107-114.

Katiyar, S.K. et al. "In Vitro Susceptibilities of the AIDS-Associated Microsporidian *Encephalitozoon intestinalis* to Albedazole, Its Sulfoxide Metabolite, and 12 Additional Benzimidazole Derivatives", Antimicrobial Agents and Chemotherapy, vol. 41 No. 12, Dec. 1997, pp. 2729-2732.

Lallo, M. A. et al. "Effect of Three Drugs against *Encephalitozoon cuniculi* Infection in Immunosuppressed Mice", Antimicrobial Agents and Chemotherapy, vol. 57 No. 7, Jul. 2013, pp. 3067-3071.

Didier, E. et al. "Screening of compounds for antimicrosporidial activity in vitro". Folia Parasitologica, vol. 45, 1998, pp. 129-139.

Franssen, F.F.J. et al. "Susceptibility of *Encephalitozoon cuniculi* to Several Drugs In Vitro". Antimicrobial Agents and Chemotherapy, vol. 39 No. 6, Jun. 1995, p. 1265-1268.

Silviera, H. et al. "In vitro cultivation of the human microsporidium *Vittaforma corneae:* development and effect of albendazole". Folia Parasitologica, vol. 42, 1995, pp. 241-250.

Groß, U. "Treatment of microsporidiosis including albendazole". Parasitol Res, vol. 90, 2003, pp. S14-S18.

Schmahl, G. et al. "Treatment of fish parasites. 11. Effects of different benzimidazole derivatives (albendazole, mebendazole, fenbendazole) on *Glugea anomala*, Moniez, 1887 (Microsporidia): ultrastructural aspects and efficacy studies", Parasitol Res, vol. 84, 1998, pp. 41-49.

International Search Report dated Jun. 27, 2017 in PCT/JP2017/013489 with English-language translation (4 pgs.).

Office Action issued in co-pending Chinese Patent Application No. 201780021272.1, dated Aug. 23, 2019.

Office Action issued in co-pending European Patent Application No. 17775503.0, dated Oct. 16, 2019.

Schmahl, et al., "Effects of Fenbendazole, Albendazole and Mebendazole on Developmental Stages of Glugea Anomala, Moniez, 1887 (Microsporidia): An Ultrastructural Investigation," *Journ. of Eukaryotic Microbilogy*, vol. 44, No. 1, p. 33A (1997).

Guo, et al., "Selected Parasitosis in Cultured and Wild Fish," *Veterinary Parasitology*, vol. 163, No. 3, pp. 207-216 (Aug. 2009).

Kent, et al., "Microsporidia in Fish," "Chapter 20" In: "Microsporidia: Pathogens of Opportunity (First Edition)," pp. 493-520 (2014).

Japan Fisheries Resources Protection Association, Mar. 2015, "Fish Disease Information Materials (Parasitic Diseases and Fungal Diseases) Additional Edition" (Table of Contents, 2. Microsporidia, Appendix of Contents, Microsporidia of Appendix, 18 pages. [English Abstract].

Saleh, "Development of a Novel in Vitro Method for Drug Development for Fish; Application to Test Efficacy of Antimicrosporidian Compounds," *Veterinary Record*, pp. 175-180 (Dec. 2014).

Third Party Observation issued in co-pending Japanese Patent Application No. 2017-47531, dated Nov. 2, 2017.

\* cited by examiner

SEQUENCE LISTING

<160> NUMBER OF SEQ ID NOS: 7

<210> SEQ ID NO 1
<211> LENGTH: 87
<212> TYPE: PRT
<213> ORGANISM: Vittaforma corneae

<400> SEQUENCE: 1

```
Pro Asp Arg Met Leu Ala Thr Phe Ser Val Val Pro Ser Pro Lys Val
1               5                   10                  15

Ser Asp Thr Val Val Glu Pro Tyr Asn Ala Thr Leu Ser Ile His Gln
            20                  25                  30

Leu Val Glu Asn Ala Asp Gln Thr Phe Cys Ile Asp Asn Asp Ala Leu
        35                  40                  45

Tyr Asp Ile Cys His Lys Thr Leu Lys Met Lys Ser Pro Gly Tyr Asp
    50                  55                  60

Gln Leu Asn His Leu Val Ser Leu Val Met Ser Gly Val Thr Thr Cys
65                  70                  75                  80

Leu Arg Phe Pro Gly Gln Leu
                85
```

<210> SEQ ID NO 2
<211> LENGTH: 87
<212> TYPE: PRT
<213> ORGANISM: Encephalitozoon cuniculi

<400> SEQUENCE: 2

```
Pro Asp Arg Met Ile Cys Thr Phe Ser Val Val Pro Ser Pro Lys Val
1               5                   10                  15

Ser Asp Thr Val Val Glu Pro Tyr Asn Ala Thr Leu Ser Ile His Gln
            20                  25                  30

Leu Val Glu Asn Ala Asp Glu Thr Phe Cys Ile Asp Asn Glu Ala Leu
        35                  40                  45

Tyr Asp Ile Cys Phe Arg Thr Leu Lys Leu Asn Asn Pro Gly Tyr Gly
    50                  55                  60

Asp Leu Asn His Leu Val Ser Leu Val Met Ser Gly Val Thr Thr Cys
65                  70                  75                  80

Leu Arg Phe Pro Gly Gln Leu
                85
```

<210> SEQ ID NO 3
<211> LENGTH: 87
<212> TYPE: PRT
<213> ORGANISM: Microsporidium seriolae

<400> SEQUENCE: 3

```
Pro Asp Arg Met Met Cys Thr Phe Ser Val Val Pro Ser Pro Lys Val
1               5                   10                  15

Ser Asp Thr Val Val Glu Pro Tyr Asn Ala Thr Leu Ser Ile His Gln
            20                  25                  30

Leu Val Glu Asn Ala Asp Glu Thr Phe Cys Ile Asp Asn Glu Ala Leu
        35                  40                  45

Tyr Asp Ile Cys Phe Arg Ser Leu Lys Leu Thr Asn Pro Gly Tyr Gly
    50                  55                  60

Asp Leu Asn His Leu Val Ser Leu Val Met Ser Gly Val Thr Thr Cys
65                  70                  75                  80

Leu Arg Phe Pro Gly Gln Leu
                85
```

<210> SEQ ID NO 4
<211> LENGTH: 87
<212> TYPE: PRT
<213> ORGANISM: Microsporidium seriolae

<400> SEQUENCE: 4

Pro Asp Arg Met Met Cys Thr Phe Ser Val Val Pro Ser Pro Lys Val
1               5                   10                  15

Ser Asp Thr Val Val Glu Pro Tyr Asn Ala Thr Leu Ser Ile His Gln
            20                  25                  30

Leu Val Glu Asn Ala Asp Glu Thr Phe Cys Ile Asp Asn Glu Ala Leu
        35                  40                  45

Tyr Asp Ile Cys Phe Arg Ser Leu Lys Leu Thr Asn Pro Gly Tyr Gly
    50                  55                  60

Asp Leu Asn His Leu Val Ser Leu Val Met Ser Gly Val Thr Thr Cys
65                  70                  75                  80

Leu Arg Phe Pro Gly Gln Leu
                85

<210> SEQ ID NO 5
<211> LENGTH: 87
<212> TYPE: PRT
<213> ORGANISM: Microsporidium seriolae

<400> SEQUENCE: 5

Pro Asp Arg Met Met Cys Thr Phe Ser Val Val Pro Ser Pro Lys Val
1               5                   10                  15

Ser Asp Thr Val Val Glu Pro Tyr Asn Ala Thr Leu Ser Ile His Gln
            20                  25                  30

Leu Val Glu Asn Ala Asp Glu Thr Phe Cys Ile Asp Asn Glu Ala Leu
        35                  40                  45

Tyr Asp Ile Cys Phe Arg Ser Leu Lys Leu Thr Asn Pro Gly Tyr Gly
    50                  55                  60

Asp Leu Asn His Leu Val Ser Leu Val Met Ser Gly Val Thr Thr Cys
65                  70                  75                  80

Leu Arg Phe Pro Gly Gln Leu
                85

<210> SEQ ID NO 6
<211> LENGTH: 87
<212> TYPE: PRT
<213> ORGANISM: Microsporidium seriolae

<400> SEQUENCE: 6

Pro Asp Arg Met Met Cys Thr Phe Ser Val Val Pro Ser Pro Lys Val
1               5                   10                  15

Ser Asp Thr Val Val Glu Pro Tyr Asn Ala Thr Leu Ser Ile His Gln
            20                  25                  30

Leu Val Glu Asn Ala Asp Glu Thr Phe Cys Ile Asp Asn Glu Ala Leu
        35                  40                  45

Tyr Asp Ile Cys Phe Arg Ser Leu Lys Leu Thr Asn Pro Gly Tyr Gly
    50                  55                  60

Asp Leu Asn His Leu Val Ser Leu Val Met Ser Gly Val Thr Thr Cys
65                  70                  75                  80

Leu Arg Phe Pro Gly Gln Leu
                85

```
<210> SEQ ID NO 7
<211> LENGTH: 87
<212> TYPE: PRT
<213> ORGANISM: Microsporidium seriolae

<400> SEQUENCE: 7

Pro Asp Arg Met Met Cys Thr Phe Ser Val Val Pro Ser Pro Lys Val
1               5                   10                  15

Ser Asp Thr Val Val Glu Pro Tyr Asn Ala Thr Leu Ser Ile His Gln
            20                  25                  30

Leu Val Glu Asn Ala Asp Glu Thr Phe Cys Ile Asp Asn Glu Ala Leu
        35                  40                  45

Tyr Asp Ile Cys Phe Arg Ser Leu Lys Leu Thr Asn Pro Gly Tyr Gly
    50                  55                  60

Asp Leu Asn His Leu Val Ser Leu Val Met Ser Gly Val Thr Thr Cys
65                  70                  75                  80

Leu Arg Phe Pro Gly Gln Leu
                85
```

COMPOSITION FOR CONTROLLING MICROSPORIDIA IN FISHES AND METHOD FOR CONTROLLING MICROSPORIDIA IN FISHES USING SAME

CROSS REFERENCE TO RELATED APPLICATIONS

This application is a national stage entry of PCT/JP2017/013489, filed Mar. 30, 2017, which claims priority to Japanese Application No. 2017-047531, filed Mar. 13, 2017, and to Japanese Application No. 2016-070840, filed Mar. 31, 2016, the disclosures of both of which are incorporated by reference herein in their entirety.

TECHNICAL FIELD

The present invention relates to a composition for controlling or preventing microsporidia in a fish or a seafood, and a method for controlling or preventing microsporidia in a fish or a seafood using the same.

BACKGROUND ART

Microsporidia are a group of single-cell eukaryotes parasitizing in cells of various animals such as insects, crustaceans, fishes, mammals, etc., and many of them show pathogenicity in these animals. As a microsporidian showing pathogenicity in a fish or a seafood, the following parasites are know:

(1) Microsporidia causing encephalomyelitis of seriola ("Kanpachi" as a Japanese name (great amberjack), "Hamachi" as a Japanese name (young yellowtail), (2) Heterosporis anguillarum causing beko disease in farmed eels, (3) Glugea plecoglossi etc. causing glugeosis in "Ayu" as a Japanese name (sweetfish), (4) *Microsporidium takedai* causing takeda microsporidiosis in rainbow trout, (5) *Microsporidium seriolae* causing beko disease in "Buri" as a Japanese name (adult yellowtail), (6) Enterocytozoon hepatopenaei as a microsporidian parasite in cultured shrimps, etc.

The beko disease of fishes belonging to a group of "Buri" is an infection of "Mojako" as a Japanese name (yellowtail larva) caused by microsporidian *Microsporidium seriolae* and is currently confirmed in Japan and Taiwan. When "Mojako" is infected with *Microsporidium seriolae*, a cheese-like massive cyst (sporangium) that can be confirmed even by the naked eye is formed in muscle. When the formation of the cyst is terminated, the surrounding muscle tissue is melted, to cause recognition of irregularities on the fish body. The beko disease generally disappears with age, but partially remains in the muscle upon shipment, which significantly reduces the product value thereof in some cases. For this reason, the aquaculturists have suffered a great economic loss. In recent years, even in the farmed "Kanpachi", occurrence of the beko disease has become a problem and the damage is tending to expand, though the type of the causative microsporidia varies.

If the beko disease is recognized in farmed "Buri" etc. after shipment, it is not only responsible for claims from consumers and requests for discounts due to rating downgrade from distributors, but also in the worst case, the aquaculturists may suffer serious blows such as suspension of trading. Further, if the weight of the fish exceeds 4 kg, it becomes difficult to judge from the appearance whether or not the fish is suffering from the beko disease, so there is no protection method upon shipment.

Although 25 or more years have elapsed since the beko disease of "Buri" has been reported, there are no effective treatment methods or treatment agents or vaccines with efficacy for the beko disease of "Buri" etc. and no control methods have been established under existing conditions. Consequently, it is a real countermeasure to keep infections at a moderate level by breeding management. It is believed that the infection of the beko disease concentrates on "Mojako" at specific season (May to August), and, since, then, the infection on "Buri" is not likely to occur. Therefore, it is the only realistic means to eliminate those showing irregularities on the surface of the body at the time of vaccination (May to June). However, in the case of elimination at the time of vaccination, there is an economic loss because of a decrease in the yield due to the disposal of the organism. Furthermore, there is no scientifically verified data on the results after the elimination, so questions remain about the effect.

It has been experimentally reported that when seawater filtered through sand was used as breeding water, the development of the beko disease was not recognized. However, considering the scale and management ability, it is virtually impossible to conduct breeding in such a condition, in outdoor fish farming sites.

Another reason for the delayed establishment of the prevention and treatment method of the beko disease is based on that the detailed life cycle of the beko disease is not clear. Further, there is no rational method for searching candidate study drugs because the method of culturing a microsporidian as a causative microorganism has not been established and a drug susceptibility test thus cannot be carried out, as a cause of the obstacle to the development of the treatment agent. In addition, it is not possible to conduct an effective infection experiment in the laboratory because the infection is not established even if a microsporidian obtained from the infected fish is inoculated directly to the other fish. As described above, the test for taking basic data for the control measures against the beko disease cannot be carried out.

Benzimidazole medicines are mentioned as medicines with high therapeutic efficacy for microsporidiosis of terrestrial animals including humans. For example, it has been reported in the antimicrobial activity test by the culture test that high antimicrobial activity of a benzimidazole medicine or fumagillin is recognized against some microsporidia. Particularly, Albendazole (see, the following formula) has been reported to exhibit high antimicrobial activity against many microsporidia (see, Non-Patent Documents 3 to 7).

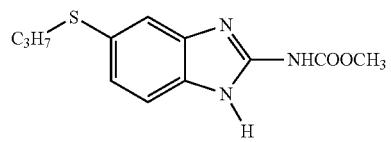

In addition, benzimidazole-based medicines containing albendazole are the first choice medicines for human microsporidiosis and rabbit encephalitozoonosis caused by a microsporidian as a causative agent (see, Non-Patent Document 8).

On the other hand, it has been reported for measures against microsporidia in fishes that, when fumagillin, an antimicrobial agent against amoeba, was administered to glugeosis of "Ayu" (causative agent is Glugea plecoglossi, which is a kind of microsporidia belonging to Apansporoblastina: see, Non-Patent Document 1) and the beko disease of eels (causative agent is Heterosporis anguillarum, which is a kind of microsporidia: see, Non-Patent Document 2), high therapeutic efficacy was recognized.

It has been reported that disintegration of pathogenic parasites was observed under a microscope, as a result of carrying out immersion bathing with benzimidazole-based substances in the case of glugeosis of "Togeuo" as a Japanese name (Gasterosteidae) caused by Glugea anomala as a causative agent. However, changes in the morphology of the protozoa under a microscope after drug sensitization have only been confirmed. In addition, Glugea anomala is a microsporidian causing a pathological condition which is clearly different from *Microsporidium* genus in *Perciformes* which makes cysts in muscle, because Glugea anomala is susceptible to drug action by immersion bathing since it produces cysts mainly on the body surface of fish (see, Non-Patent Document 9).

Benzimidazole medicines are approved as a livestock drug and a human drug against parasitic diseases in many countries. Also in Japan as our country, human drugs: Eskazole (main ingredient: albendazole) as an echinococcus control agent; livestock drugs: Fasinex (main ingredient: triclabendazole) as a fasciola hapatica control agent and Flumoxal (main ingredient: flubendazole) and Maypole (main ingredient: fenbendazole) as a roundworm, strongyle and whipworm control agent; and fishery drugs: Marinbantel (main ingredient: fenbendazole (see, the following formula)) against "Eramushi" as a Japanese name as Japanese tiger puffer (heterobothriosis); are commercially available.

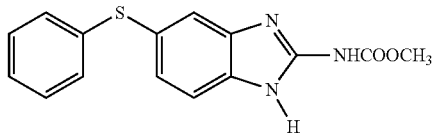

PRIOR ART DOCUMENTS

Non-Patent Documents

Non-Patent Document 1: Sei Takahashi and Shozo Egusa, "Studies on glugeosis of "Ayu"—II: Review of the Control Method (1), Effect of Fumagillin Oral Administration", Fish Disease Research (Japanese Society of Fish Pathology), Vol. 11 (1976-1977), No. 2, pp. 83-88.

Non-Patent Document 2: Terumasa Kano, Tetsuo Okuchi and Akio Fukui, "Studies on Pleistophora disease of eel—II: Method and Effect of Fumagillin Administration", Fish Disease Research (Japanese Society of Fish Pathology), Vol. 17 (1982), pp. 107-114.

Non-Patent Document 3: Katiyar S K, in vitro susceptibilities of the AIDS-associated microsporidian Encephalitozoon intestinalis to albendazole, its sulfoxide metabolite, and 12 additional benzimidazole derivatives. Antimicrob Agents Chemother. 1997 December; 41 (12): 2729-32.

Non-Patent Document 4: Lallo M A, da Costa L F, de Castro J M. Effect of three drugs against Encephalitozoon cuniculi infection in immunosuppressed mice. Antimicrob Agents Chemother. 2013 July; 57 (7): 3067-71.

Non-Patent Document 5: Didier E S, Maddry J A, Kwong C D, Green L C, Snowden K F, Shadduck J A. Screening of compounds for antimicrosporidial activity in vitro. Folia Parasitol (Praha). 1998; 45 (2): 129-39.

Non-Patent Document 6: Franssen F F, Lumeij J T, van Knapen F. Susceptibility of Encephalitozoon cuniculi to several drugs in vitro. Antimicrob Agents Chemother. 1995 June; 39 (6): 1265-8.

Non-patent document 7: Silveira H, Canning E U. In vitro cultivation of the human microsporidium Vittaforma corneae: development and effect of albendazole. Folia Parasitol (Praha). 1995; 42 (4): 241-50.

Non-Patent Document 8: Gross U. treatment of microsporidiosis including albendazole. Parasitol Res. 2003 June; 90 Supp 1: 14-80. Epub 2002 Dec. 10.

Non-Patent Document 9: Schmahl G, Benini J. Treatment of fish parasites. Effects of different benzimidazole derivatives (albendazole, mebendazole, fenbendazole) on Glugea anomala, Moniez, 1887 (Microsporidia): ultrastructural aspects and efficacy studies. Parasitol Res. 1998; 84 (1): 41-9.

SUMMARY OF THE INVENTION

Problem to be Solved by the Invention

However, fumagillin has not been approved as a human drug or a livestock drug because its safety to animals is low. Also for benzoimidazole derivatives, changes in the morphology of the protozoa under a microscope after drug sensitization to glugeosis of "Togeuo" have only been confirmed. In addition, Glugea anomala is susceptible to drug action by immersion bathing, because it produces cysts mainly on the body surface of fishes. Glugea anomala is a microsporidian causing a pathological condition, which is clearly different from *Microsporidium* genus in *Perciformes* which makes cysts in muscle. For this reason, it is not an exaggeration to say that for aquaculture projects, there is absolutely no information on the control effect against infection with *Microsporidium* genus of *Perciformes*, which is the most important, from the viewpoint of productivity.

The present invention has been completed in view of such circumstances described above, and has an object to provide a composition for controlling or preventing microsporidia in a fish or a seafood, which prevents microsporidian infection in the muscle or organs of a fish or a seafood; and/or which suppresses the growth of microsporidia in the muscle or organs of a fish or a seafood; and/or which is highly effective in eliminating microsporidia from the bodies of a fish or a seafood; and also which is excellent in safety. An object of the present invention is to provide a method of controlling or preventing microsporidia in a fish or a seafood using the composition, which can be used effectively in industry.

Means for Solving the Problem

The first embodiment of the present invention according to the above object provides a composition for controlling or preventing microsporidia in a fish or a seafood, to solve the above-described problem, which comprises, as an active ingredient, one or more compounds selected from the group consisting of:

the compounds represented by the following chemical formula (I), which prevent microsporidian infection in the muscle or organs of the fish or the seafood, and/or which suppress the growth of microsporidia in the muscle or organs of the fish or the seafood, and/or which have an activity for eliminating microsporidia from the body of the fish or the seafood;

the pharmaceutically acceptable salts of the compounds of the following chemical formula (I); and the compounds generating the compounds represented by the following chemical formula (I) by metabolism in the body of the fish or the seafood.

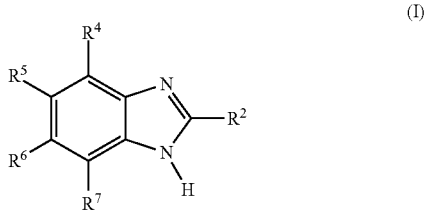

(I)

In the above-described chemical formula (I), each substituent has the following meanings:

$R^2$ is a functional group selected from the group consisting of an amino group, a functional group represented by the formula —NH—COOR$^8$, a functional group represented by the formula —N═CHR$^9$, a functional group represented by the formula —N═CR$^{10}$(R$^{11}$), a 2-thiazolyl group and an alkylthio group.

$R^4$, $R^6$ and $R^7$ are each independently an atom or a functional group selected from the group consisting of a hydrogen atom, a halogen atom, a nitro group, a sulfonic acid group, a carboxyl group, a cyano group, an acyl group, an alkyl group, a cycloalkyl group, an alkoxyl group, an aryl group, a heteroaryl group, an aryloxy group, a heteroaryloxy group, a substituted acyl group, a substituted alkyl group, a substituted cycloalkyl group, a substituted alkoxyl group, a substituted aryl group, a substituted heteroaryl group, a substituted aryloxy group and a substituted heteroaryloxyl group.

$R^5$ is an atom or a functional group selected from the group consisting of a hydrogen atom, an amino group, a functional group represented by the formula —NH—COOR$^{12}$, an alkoxyl group, an alkylthio group, an arylthio group, an alkyl sulfoxide group (alkylsulfinyl group), an aryl sulfoxide group (arylsulfinyl group), an acyl group, a substituted alkoxyl group, a substituted alkylthio group, a substituted alkyl sulfoxide group (substituted alkylsulfinyl group), a substituted aryl sulfoxide group (substituted arylsulfinyl group), a substituted acyl group, a halogen group, an aryloxy group, a substituted aryloxy group and $R^{13}$—CO—NH— ($R^{13}$ is alkyl group).

$R^8$, $R^9$, $R^{10}$, $R^{11}$ and $R^{12}$ are each independently an atom or a functional group selected from the group consisting of an alkyl group, a cycloalkyl group, an alkoxyl group, an aryl group, a heteroaryl group, a substituted acyl group, a substituted alkyl group, a substituted cycloalkyl group, a substituted alkoxyl group, a substituted aryl group and a substituted heteroaryl group.

The second embodiment of the present invention provides a method of controlling or preventing microsporidia in a fish or a seafood, which comprises a step of administering to the fish or the seafood a composition comprising, as an active ingredient, one or more compounds selected from the group consisting of compounds represented by the above-described chemical formula (I), which prevent microsporidian infection in the muscle or organs of the fish or the seafood, and/or which suppress the growth of microsporidia in the muscle or organs of the fish or the seafood, and/or which have activity for eliminating microsporidia from the body of the fish or the seafood; pharmaceutically acceptable salts thereof; and compounds generating the compounds represented by the chemical formula (I) by metabolism in the body of the fish or the seafood, in order to solve the above-described problem.

In the composition for controlling or preventing microsporidia in a fish or a seafood according to the first embodiment of the present invention and the method of controlling or preventing microsporidia in a fish or a seafood according to the second embodiment of the present invention, the compounds represented by the above-described chemical formula (I) may be any of compounds represented by the formulae (1) to (7) and (10) described below; and the compounds generating the compounds represented by the above-described chemical formula (I) may be any of compounds represented by the formulae (8) and (9) described below.

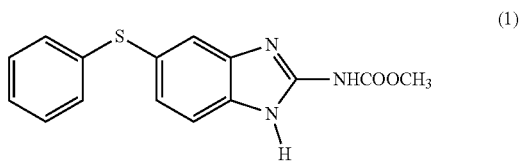

(1)

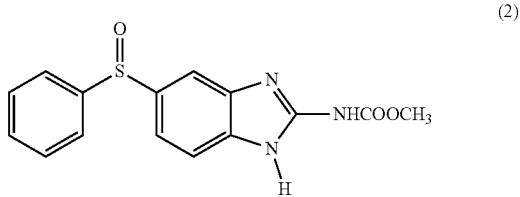

(2)

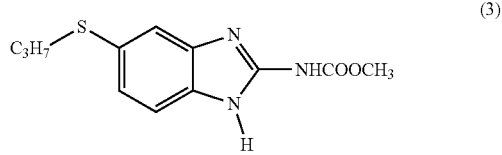

(3)

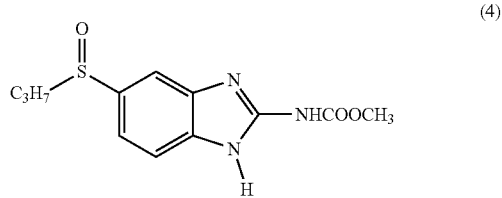

(4)

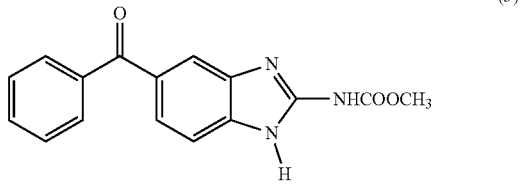

(5)

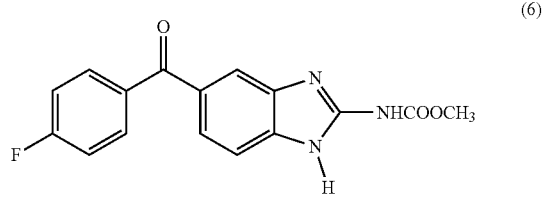

(6)

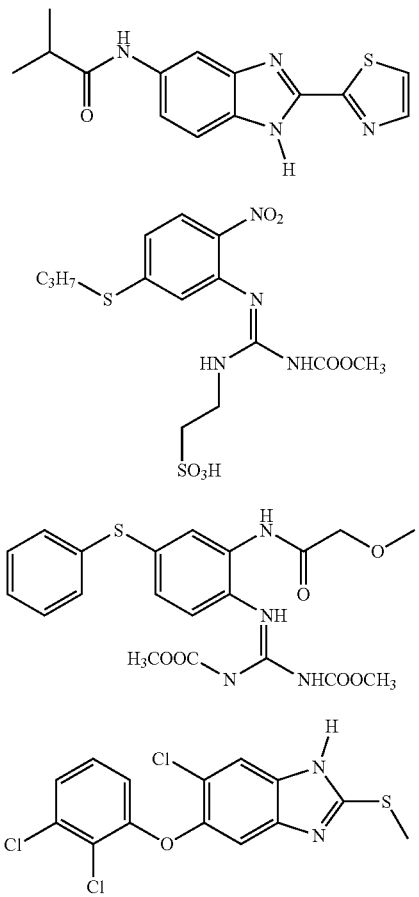

In the composition for controlling or preventing microsporidia in a fish or a seafood according to the first embodiment of the present invention and the method of controlling or preventing microsporidia in a fish or a seafood according to the second embodiment of the present invention, the above-described fish or seafood as fishery products or an aquatic life, and as a live subject to be treated, may be a fish, for example, belonging to *Perciformes* or Pleuronectiformes.

In the composition for controlling or preventing microsporidia in a fish or a seafood according to the first embodiment of the present invention and the method of controlling or preventing microsporidia in a fish or a seafood according to the second embodiment of the present invention, the above-described fish or seafood, as an aquatic life and as a live subject to be treated, may be a fish belonging to the genus *Thunnus* of *Perciformes Scombridae*, the genus *Seriola* of *Perciformes Carangidae*, the genus *Chrysophrys* of *Perciformes sparidae*, the genus *Paralichthys* of Pleuronectiformes Paralichthyidae or the genus *Verasper* of Pleuronectiformes Pleuronectidae.

In the composition for controlling or preventing microsporidia in a fish or a seafood according to the first embodiment of the present invention and the method of controlling or preventing microsporidia in a fish or a seafood according to the second embodiment of the present invention, the above-described microsporidia may be, for example, microsporidia belonging to the *Microsporidium* genus.

In the composition for controlling or preventing microsporidia in a fish or a seafood according to the first embodiment of the present invention and the method of controlling or preventing microsporidia in a fish or a seafood according to the second embodiment of the present invention, the above-described microsporidia may be *Microsporidium seriolae*.

In the composition for controlling or preventing microsporidia in a fish or a seafood according to the first embodiment of the present invention, the composition may be, for example, any of an oral administration agent, a feed for fish farming, an injection agent and an immersion bathing agent.

In the present invention, "control or prevention of microsporidia" includes the meanings of prevention of microsporidian infection, prevention of the growth of microsporidia invaded into the body of the fish or the seafood (by infection), elimination or prevention of invasion of microsporidia into the muscle or organs of the other fish or the other seafood; or management of the number of individuals (including also elimination and killing).

In the method for controlling or preventing microsporidia in a fish or a seafood according to the second embodiment of the present invention, the administration to a fish or a seafood may be oral administration. In this case, the composition for controlling or preventing microsporidia in a fish or a seafood according to the first embodiment of the present invention, as an oral agent, may be orally administered in a single dose or in multiple doses at intervals of not less than 1 day and not more than 180 days, so that one dose of the active ingredient is 0.1 mg/kg or more and 100 mg/kg or less, to prevent microsporidian infection in a fish or a seafood. The composition for controlling or preventing microsporidia in a fish or a seafood according to the first embodiment of the present invention, as an oral agent, may be orally administered in a single dose; or multiple doses at intervals of not less than 6 hours and not more than 180 days, so that one dose of the active ingredient is 20 mg/kg or more and 400 mg/kg or less, to eliminate or prevent microsporidia in a fish or a seafood.

In the method for controlling or preventing microsporidia in a fish or a seafood according to the second embodiment of the present invention, the composition for controlling or preventing microsporidia in a fish or a seafood according to the first embodiment of the present invention, as an oral agent, may be orally administered multiple doses at intervals of not less than 3 days and not more than 180 days, so that one dose of the active ingredient is 20 mg/kg or more and 400 mg/kg or less, to eliminate microsporidia in a fish or a seafood or to prevent reinfection. In this case, the composition may be orally administered at intervals of not less than 5 days and not more than 21 days, alternatively, the above-described multiple oral administration may be taken as one cycle and the cycle may be repeated at intervals of not less than 3 days and not more than 180 days.

In the method of controlling or preventing microsporidia in a fish or a seafood according to the second embodiment of the present invention, the above-described administration to a fish or a seafood may be intramuscular injection or intraperitoneal injection.

In the method of controlling or preventing microsporidia in a fish or a seafood according to the second embodiment of the present invention, the above-described administration to a fish or a seafood may be immersion administration in an immersion bath. In this case, immersion administration to a fish or a seafood may be carried out in an immersion bathing solution containing the composition for controlling or preventing microsporidia in a fish or a seafood according to the first embodiment of the present invention as an immersion bathing agent, so that the concentration of its active ingredient is 1 ppm to 1000 ppm.

Effect of the Invention

According to the present invention, a composition for controlling or preventing microsporidia in a fish or a seafood is provided, which prevents microsporidian infection in the muscle or organs of a fish or a seafood; and/or which suppresses the growth of microsporidia in the muscle or organs of a fish or a seafood; and/or which is highly effective in eliminating microsporidia from the body of a fish or a seafood; and also which is excellent in safety; and a method for controlling or preventing microsporidia in a fish or a seafood using the composition is also provided.

MODES FOR CARRYING OUT THE INVENTION

Next, concrete embodiments of the present invention will be described, for understanding of the invention.

First Embodiment

The composition for controlling or preventing microsporidia in a fish or a seafood according to the first embodiment of the present invention is hereinafter referred to as "composition for controlling microsporidia in a fish or a seafood" or abbreviated simply as "composition" in some cases.

The composition comprises, as an active ingredient, one or more compounds selected from the group consisting of: the compounds represented by the following chemical formula (I), which prevent microsporidian infection in the muscle or organs of a fish or a seafood, and/or which suppress the growth of microsporidia in the muscle or organs of the fish or the seafood, and/or which have activity for eliminating microsporidia from the body of the fish or the seafood;
pharmaceutically acceptable salts thereof, and
compounds generating the compounds represented by the chemical formula (I) by metabolism in the body of the fish or the seafood (i. e., prodrugs).

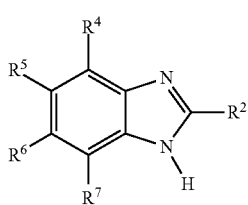

(I)

In the above-described chemical formula (I), each subsistent has the following meaning:

$R^2$ is a functional group selected from the group consisting of an amino group, a functional group represented by the formula —NH—COOR$^8$, a functional group represented by the formula —N=CHR$^9$, a functional group represented by the formula —N=CR$^{10}$(R$^{11}$), a 2-thiazolyl group and an alkylthio group.

$R^4$, $R^6$ and $R^7$ are each independently an atom or a functional group selected from the group consisting of a hydrogen atom, a halogen atom, a nitro group, a sulfonic acid group, a carboxyl group, a cyano group, an acyl group, an alkyl group, a cycloalkyl group, an alkoxyl group, an aryl group, a heteroaryl group, an aryloxy group, a heteroaryloxy group, a substituted acyl group, a substituted alkyl group, a substituted cycloalkyl group, a substituted alkoxyl group, a substituted aryl group, a substituted heteroaryl group, a substituted aryloxy group and a substituted heteroaryloxy group.

$R^5$ is an atom or a functional group selected from the group consisting of a hydrogen atom, an amino group, a functional group represented by the formula —NH—COOR$^{12}$, an alkoxyl group, an alkylthio group, an arylthio group, an alkyl sulfoxide group (alkylsulfinyl group), an aryl sulfoxide group (arylsulfinyl group), an acyl group, a substituted alkoxyl group, a substituted alkylthio group, a substituted alkyl sulfoxide group (substituted alkylsulfinyl group), a substituted aryl sulfoxide group (substituted arylsulfinyl group), a substituted acyl group, a halogen group, an aryloxy group, a substituted aryloxy group and R$^{13}$—CO—NH— (R$^{13}$ is alkyl group).

$R^8$, $R^9$, $R^{10}$, $R^{11}$ and $R^{12}$ are each independently an atom or a functional group selected from the group consisting of an alkyl group, a cycloalkyl group, an alkoxyl group, an aryl group, a heteroaryl group, a substituted acyl group, a substituted alkyl group, a substituted cycloalkyl group, a substituted alkoxyl group, a substituted aryl group and a substituted heteroaryl group.

As the substituted or unsubstituted alkyl group in the above-described chemical formula (I), the alkyl groups have preferably 1 to 6 carbon atoms and more preferably 1 to 3 carbon atoms.

The alkyl groups contained in the substituted or unsubstituted alkylthio group, the substituted or unsubstituted acyl group, the substituted or unsubstituted alkoxyl group and the substituted or unsubstituted alkyl sulfoxide group (alkylsulfinyl group) in the above chemical formula (I) have each independently preferably 1 to 6 carbon atoms, more preferably 1 to 3 carbon atoms.

As the substituted or unsubstituted cycloalkyl group, the cycloalkyl group has preferably 3 to 7 carbon atoms.

As the substituted or unsubstituted aryl group in the above chemical formula, a phenyl group is preferred.

As the aryl group in the substituted or unsubstituted aryloxy group, the substituted or unsubstituted acyl group, the substituted or unsubstituted arylthio group and the substituted or unsubstituted aryl sulfoxide group (arylsulfanyl group) in the above-described chemical formula (I), a phenyl group is preferred.

Examples of the substituent of the aryl group include a halogen atom.

Examples of the substituted phenyl group include a 4-fluorophenyl group and a 2,3-dichlorophenyl group.

Examples of the acyl group having a substituted or unsubstituted aryl group include a phenylcarbonyl group and a 4-fluorophenylcarbonyl group.

Examples of the substituted aryloxy group include a 2,3-dichlorophenyloxy group.

Examples of the alkylthio group include a methylsulfanyl group, an ethylsulfanyl group, and a propylsulfanyl group.

Examples of the arylthio group include a phenylthio.

Examples of the alkyl sulfoxide group (alkylsulfinyl group) include a methylsulfinyl group, an ethylsulfinyl group, and a propylsulfinyl group.

Examples of the aryl sulfoxide group (arylsulfinyl group) include a phenylsulfinyl group.

Benzimidazole compounds comprise a benzene-imidazole complex ring (benzimidazole ring) as is shown in the chemical formula (I) described above, and it is deemed that this skeleton strongly binds to tubulin in cells of nematodes and microsporidia, thereby inhibiting the polymerization action of the microtubules in the cell, to exert anthelmintic action. The difference of the antimicrobial activity depending on the difference of the functional group on the side chain is recognized (Reference: E. Lacey. Mode of action of benzimidazoles. Parasitology Today 1990, 6, pp. 112-115.).

Examples of the active ingredient of the controlling or preventing composition include benzimidazole derivatives; pharmaceutically acceptable salts thereof in the case of the benzimidazole derivatives have a basic functional group such as an amino group etc. or an acidic functional group such as a carboxylic acid group, a sulfonic acid group etc. as the substituent; and compounds generating the benzimidazole derivatives or their pharmaceutically acceptable salts by metabolism in the body of a fish or a seafood, which may not necessarily contain a benzimidazole ring. The active ingredient may be one of these, or it may be a mixture comprising any two or more of them in any proportion.

Concrete examples of the pharmaceutically acceptable salts include alkali metal salts such as a sodium salt, a potassium salt etc.; alkaline earth metal salts such as a magnesium salt, a calcium salt etc.; an ammonium salt; organic acid salts such as a salt with acetic acid, a salt with propionic acid, a salt with butyric acid, a salt with lactic acid, a salt with tartaric acid, a salt with citric acid, a salt with succinic acid, a salt with fumaric acid, a salt with maleic acid, etc.; and inorganic acid salts such as a hydrochloride, a nitrate salt, a sulfate salt, a hydrogen sulfate salt, a carbonate salt, a hydrogen carbonate salt etc.

Preferable examples of the compound represented by the chemical formula (I), the pharmaceutically acceptable salts thereof and the compound (prodrug) generating the compound represented by the chemical formula (I) include compounds represented by the formulae (1) to (10) described below.

The compound represented by the formula (8) is a prodrug of albendazole, and the compound represented by the formula (9) is a prodrug of fenbendazole.

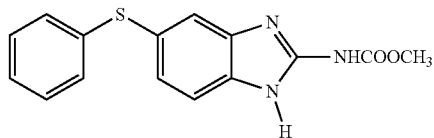

(1)

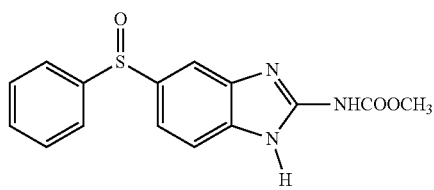

(2)

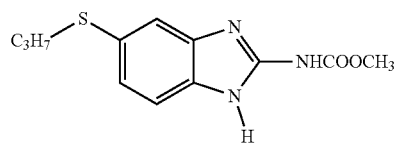

(3)

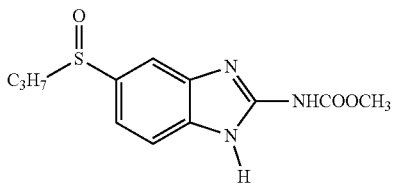

(4)

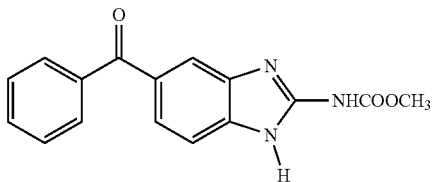

(5)

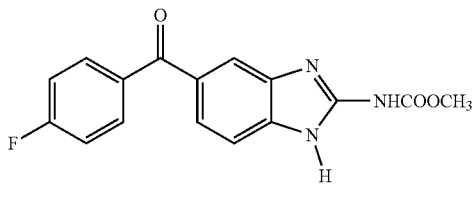

(6)

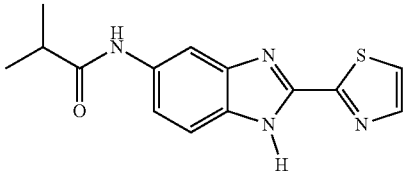

(7)

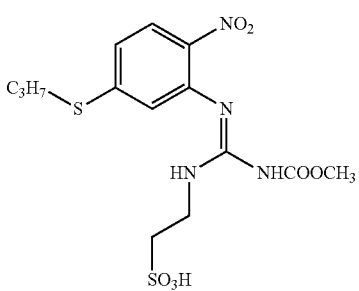

(8)

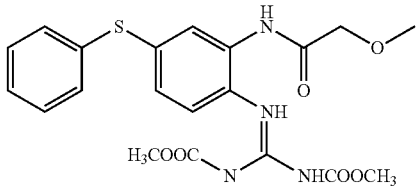

(9)

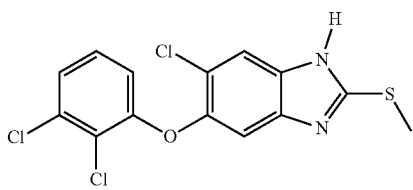

(10)

Particularly preferred compounds in the above compounds are fenbendazole represented by the formula (1), albendazole represented by the formula (3), flubendazole represented by the formula (6) and triclabendazole represented by the formula (10).

The fish or seafood of interest are not particularly limited, but are, for example, fishes belonging to *Perciformes* or Pleuronectiformes can be mentioned, Examples of the fishes include, in particular, "Kuromaguro" as a Japanese name (bluefin tuna), "Minamimaguro" as a Japanese name (southern bluefin tuna), "Mebachi" as a Japanese name (bigeye tuna), "Kihada" as a Japanese name (yellowfin tuna) etc. belonging to Perciformes-Scombridae-*Thunnus*; "Buri" as a Japanese name (adult yellowtail), "Kanpachi" as a Japanese name (great amberjack) and "Hiramasa" as a Japanese name (*Seriola lalandi*) belonging to Perciformes-Carangidae-*Seriola*; "Madai" as a Japanese name (*Pagrus major*) and "Aoboshimadai" as a Japanese name (*Pagrus caeruleostictus*) belonging to Perciformes-Sparidae-Chrysophrys; "Hirame" as a Japanese name (Japanese flounder) belonging to Pleuronectiformes-Paralichthyidae-Paralichthys; and "Hoshigarei" as a Japanese name (*Verasper variegatus*) belonging to Pleuronectiformes-Pleuronectidae-Verasper.

The microsporidia of interest are not particularly limited, but are, for example, those belonding to *Microsporidium* genus, and in particularly, *Microsporidium seriolae*, as a pathogen of the beko disease of "Buri", is mentioned.

The composition for controlling or preventing microsporidia may be formulated in any form suitable for administration to a fish or a seafood, and specific examples thereof include an oral agent, an injection agent and an immersion bathing agent. These compositions may contain at least one ingredient other than the active ingredient(s), selected from any pharmaceutically acceptable carriers, solvents, excipients, spreading agents and other additives. Known or conventional carriers, solvents, excipients, spreading agents and other additives may be used.

As described above, at least one compound selected from the group consisting of the compounds represented by the chemical formula (I), pharmaceutically acceptable salts thereof and the compounds generating the compounds represented by the chemical formula (I) can be used as an active ingredient of the composition for controlling or preventing microsporidia. Therefore, at least one compound selected from the group consisting of the compounds represented by the chemical formula (I), pharmaceutically acceptable salts thereof and the compounds generating the compounds represented by the chemical formula (I) can be used, as an active ingredient, in production of the composition for controlling or preventing microsporidia. In production of the composition for controlling or preventing microsporidia, at least one ingredient other than the active ingredient(s), can be blended to the composition. Such ingredient can be selected from any pharmaceutically acceptable carries, solvents, excipients, spreading agents and other additives described above. Therefore, the present invention includes a use method of such active ingredients in production of the composition for controlling or preventing microsporidia.

Second Embodiment

The method of controlling or preventing microsporidia in a fish or a seafood according to the second embodiment of the present invention is hereinafter referred to as "method for controlling or preventing microsporidia in a fish or a seafood" or abbreviated simply as "control or prevention method" in some cases.

The method of controlling or preventing microsporidia in a fish or a seafood comprises a step of administering, to the fish or the seafood, one or more compounds selected from the group consisting of the compounds represented by the above-described chemical formula (I), which prevent microsporidian infection in the muscle or organs of the fish or the seafood, and/or which suppress the growth of microsporidia in the muscle or organs of the fish or the seafood, and/or which have activity for eliminating microsporidia from the body of the fish or the seafood; pharmaceutically acceptable salts thereof; and the compounds generating the compounds represented by the chemical formula (I) by metabolism in the body of the fish or the seafood. Explanations of items overlapping the explanations of the composition for controlling microsporidia in fishes or seafoods according to the first embodiment of the present invention will be omitted.

Any administration methods can be used without particular restriction as long as they can be applied to a fish or a seafood, by administering the composition for controlling or preventing microsporidia to the fish or the seafood. Concrete examples of the administration method include oral administration, injection (intramuscular injection, intraperitoneal injection), immersion bathing, etc.

In the case of oral administration, the composition can be administered in any form suitable for oral administration. It is convenient and easy, and, preferable, to allow the subject to take the composition together with a feed in a form containing the composition added, at a time of feeding. The administration amount, administration interval and administration period are adjusted appropriately depending on the targeted fish or seafood; the type of microsporidia to be controlled or prevented; and the purpose of administration, for example, prevention, e.g., prevention of infection, elimination, etc. For example, in the case of microsporidian prevention, the composition for controlling or preventing microsporidia in a fish or a seafood is orally administered in a single dose or multiple doses at intervals of not less than 1 day and not more than 180 days so that one dose of the active ingredient is 0.1 mg/kg or more and 100 mg/kg or less. By administering the composition for controlling or preventing microsporidia in a fish or a seafood at such doses and intervals, the effect of preventing infection with microsporidia continues for at least 4 weeks after the end of the administration.

In the case of elimination of microsporidia, the composition is orally administered in a single dose or multiple doses at intervals of not less than 6 hours and not more than 180 days so that one dose of the active ingredient is 20 mg/kg or more and 400 mg/kg or less. In the case of administering multiple doses, the dosage may be varied for each dose, and the interval between doses may be constant or not be constant.

In the case of elimination of microsporidia and prevention of reinfection, the composition for controlling or preventing microsporidia in a fish or a seafood may be administered orally multiple times at intervals of not less than 3 days and not more than 180 days, more preferably not less than 5 days and not more than 21 days so that one dose of the active ingredient is 20 mg/kg or more and 400 mg/kg or less. When the composition for controlling or preventing microsporidia in a fish or a seafood is administered at such doses and intervals, the amount of the composition for controlling or preventing microsporidia in a fish or a seafood per one operation is larger. However, it is expected that the fish or the seafood acquire immunity against microsporidia during each administration; and that the effect of preventing reinfection of microsporidia continues for a long period of time; and that the total administration amount of the composition for controlling or preventing microsporidia in the fish or the seafood can be reduced. In this case, the above-described multiple oral administration may be taken as one cycle and the cycle may be repeated at intervals of not less than 3 days and not more than 180 days.

In the case of administration by immersion bathing, the concentration of the active ingredient in the immersion bathing solution is, for example, 0.1 ppm to 1000 ppm. The most favorable concentration and time are 10 mg/kg for 2 hours, but the effect and toxicity vary depending on water temperature, thus, it is necessary to adjust them by observing the condition of the fish to be administered. The administration may be conducted singly or multiple times. The concentration of the active ingredient in the immersion bathing solution, the immersion time for each operation, and the interval between doses are appropriately adjusted depending on the condition of drug metabolism in the fish of interest. The administration interval may be constant or may be varies for each time in the same way as the case of oral administration.

In the case of intramuscular or intraperitoneal injections, the concentration of the active ingredient in the injection solution is, for example, 1 mg/kg to 300 mg/kg. The solution may be administered in single or multiple doses, with the most preferred concentration being 10 mg/kg to 100 mg/kg. The concentration of the active ingredient and the interval of administration may be constant or may be varied for each time, in the same way as the case of oral administration. In order to maintain the blood concentration continuously for a long period of time, it is desirable to use it together with coconut oil, an adjuvant, etc.

EXAMPLES

Next, the working examples conducted for confirming the action and effect of the present invention will be described.

Example 1: Beko Disease Preventing Test 1-1: Prevention Test of Beko Disease in "Mojako" Using Fenbendazole The prevention test was conducted according to the following procedure.

Test cage: 5 m×5 m×5 m
Test number: Live 1000 fishes (each initial body weight: 12 g)
Administration method: oral administration (feed together with spreading agent)
Test period: 6 weeks
Drug used: fenbendazole (compound represented by the above-described formula (1))
Administration amount: 20 mg/kg Bw (20 mg per kg of fish body weight)
Interval between administration: 6 times/week A sampling test was carried out according to the following procedure:

Six weeks after the start of administration, each 10 fishes of "Mojako" were taken out from each test group (a control group (the test was conducted under the same conditions as the above-described test conditions, except that the feed fed contained no fenbendazole) and a fenbendazole group), and each fish was cut into three pieces. It was then visually tested whether the microsporidian cyst (beko cyst) was found in the pieces. When the beko cyst was observed, it was judged as positive and the results were accumulated. Regarding the beko cyst that could be confirmed with the naked eye, the number was confirmed and the average infection number per one fish was determined.

Table 1 shows the test results.

TABLE 1

|  | Number of tests | Number of positive fishes | Number of Beko cyst | Positive average per fish |
|---|---|---|---|---|
| Control group | 10 | 8 | 80 | 8.0 ± 5.20 |
| Fenbendazole group | 10 | 6 | 30 | 3.5 ± 3.83* |

*$p < 0.05$

Regarding the number of the infected fish, the positive number in the control group was 8 out of 10, whereas the positive number in the fenbendazole group was 6 out of 10, and no significant difference was found. In contrast, the average number of the beko cyst per one fish was 8.0±5.20 for the control group, while 3.5±3.83 for the fenbendazole group, that is, a significant difference was observed with a risk ratio within 5%.

1-2. Prevention Test of Beko Disease in "Mojako" Using Flubendazole

A preliminary test was carried out according to the following procedure:

Test cage: 5 m×5 m×5 m
Test number: Live 1000 fishes (each initial body weight: 12 g)
Administration method: oral administration (feed together with spreading agent)
Test period: 4 weeks
Drug used: flubendazole (compound represented by the above-described formula (6))
Administration amount: 20 mg/kg Bw (20 mg per kg of fish body weight)
Administration interval: 6 times/week
Sampling test procedure: same as above 1-1
Table 2 shows the test results.

TABLE 2

|  | Number of tests | Number of positive fishes | Number of Beko cyst | Positive average per fish |
|---|---|---|---|---|
| Control group | 10 | 7 | 37 | 3.9 ± 2.9 |
| Flubendazole group | 10 | 5 | 10 | 1.0 ± 1.1* |

*$p < 0.05$

As for the number of the infected fish, positive was observed in 7 out of 10 in the control group, whereas positive was observed in 5 out of 10 in the flubendazole group, and no significant difference was found as a result. In contrast, the average number of the beko cyst per fish was 3.9±2.9 for the control group, whereas 1.0±1.1 for the flubendazole group. As a result, a significant difference with a risk ratio within 5% was recognized between the control group and the flubendazole group.

1-3. Prevention Test Using Albendazole (1)

A preliminary test was carried out according to the following procedure:

Test cage: 5 m×5 m×5 m
Test number: Live 1000 fishes (each initial body weight: 7 g)
Administration method: oral administration (feed together with spreading agent)
Test period: 2 months
Drug used: albendazole (compound represented by the above-described formula (3))

Administration amount: 20 mg/kg Bw (20 mg per kg of fish body weight)

Administration interval: 6 times/week

A sampling test was carried out according to the following procedure:

Every two weeks from the start of administration, each 20 fishes of "Mojako" were taken out from each test group (100 fishes of "Mojako" at 8 weeks after the start of administration) and each fish was cut into three pieces. It was then visually tested whether the microsporidian cyst (beko cyst) was found in the pieces. When the beko cyst was observed, it was judged as positive and the test results were accumulated. Regarding the beko cyst that could be confirmed with the naked eye, the number was confirmed and the average infection number per one fish was determined.

Table 3 shows the test results.

TABLE 3

|  | 2 week | 4 weeks | 6 weeks | 8 weeks | Total |
|---|---|---|---|---|---|
| Control group | 0/20 | 4/20 | 5/20 | 29/100 | 38/160 |
| Albendazole group | 0/20 | 0/20 | 0/20* | 0/100** | 0/160** |

*p < 0.05
**p < 0.01

As for the number of infections, positive was recognized in 38 out of 160 in the control group, while no positive was found in 160 specimens in the albendazole group. As a result, a surprisingly high preventive effect was observed that the number of generation of the beko disease was 0 in the aquacultured fishes in the present test.

Table 4 shows the changes in the weight of "Mojako" used for the test.

TABLE 4

|  | 0 week | 2 weeks | 4 weeks | 6 weeks | 8 weeks |
|---|---|---|---|---|---|
| Albendazole group | 7 ± 0.53 | 18 ± 2.38 | 29 ± 4.16 | 51 ± 7.13 | 73 ± 12.6 |
| Control group | 7 ± 0.66 | 16 ± 1.66 | 26 ± 3.66 | 42 ± 5.22 | 58 ± 8.66 |

As a result of the present test, a significant increase in body weight was observed in the albendazole group as compared with the control group. The reason for this is supposed that since the beko disease did not develop, the fish grew smoothly without receiving any stress. In the albendazole group in the administration period, both an increase in the number of deaths and decline in food intake with respect to the control group were not recognized. This result shows that albendazole does not exert a harmful influence on the growth of "Mojako".

1-4. Prevention Test Using Albendazole (2)

Albendazole administration and a sampling test were carried out in the same procedure as in the above-described 1-3 except that the administration amount of albendazole was reduced to 5 or 10 mg/kg Bw. In the 10 mg/kg administration group, the number of (positive) individuals showing generation of the beko cyst was 0 out of 100 fishes of "Mojako" at 8 weeks after the start of administration. When the administration amount of albendazole was reduced to 5 mg/kg Bw, generation of the beko cyst was confirmed in 3 out of 100 fishes of "Mojako" at 8 weeks after the start of administration. When the administration amount of albendazole was 5 mg/kg Bw, generation of the beko cyst cannot be completely suppressed, however, generation of the beko cyst is suppressed significantly as compared with the control group.

1-5. Prevention Test Using Albendazole (3)

Administration of albendazole was continued for 16 weeks and a sampling test was performed at 2 weeks, 4 weeks, 6 weeks, 8 weeks, 12 weeks and 16 weeks after the start of administration in the same procedure as in the above-described 1-3. The sampling test was carried out in the same procedure also at 4 weeks after the termination of administration of albendazole (20 weeks after the start of administration).

Table 5 shows the results of the sampling test and Table 6 shows the accumulated results of the infection rates obtained through the entire 16-week period, respectively.

TABLE 5

|  |  | Positive | Negative | Infection rate |
|---|---|---|---|---|
| 2 Weeks | Control group | 0 | 20 | 0% |
|  | Albendazole group | 0 | 20 | 0% |
| 4 Weeks | Control group | 4 | 16 | 20% |
|  | Albendazole group | 0 | 20 | 0% |
| 6 Weeks | Control group | 5 | 15 | 25% |
|  | Albendazole group | 0 | 20 | 0%* |
| 8 Weeks | Control group | 29 | 71 | 29% |
|  | Albendazole group | 0 | 100 | 0%** |
| 12 Weeks | Control group | 16 | 24 | 40% |
|  | Albendazole group | 0 | 40 | 0%** |
| 16 Weeks | Control group | 15 | 32 | 47% |
|  | Albendazole group | 0 | 46 | 0%** |
| 20 Weeks | Control group | 6 | 14 | 30% |
|  | Albendazole group | 0 | 30 | 0%** |

*p < 0.05
**p < 0.01

TABLE 6

|  | Total until 16 weeks | | |
|---|---|---|---|
|  | Positive | Negative | Infection rate |
| Control group | 69 | 178 | 28% |
| Albendazole group | 0 | 246 | 0%** |

**p < 0.01

In the albendazole group, the beko cyst was not recognized in all sampled fishes during the period of administration of albendazole. This result suggests that when administration of albendazole is continued, the beko disease can be prevented almost perfectly. No generation of the beko cyst was recognized, also in "Mojako" subjected to the sampling test at 4 weeks after the termination of administration. It was confirmed from this result that the effect of preventing infection with microsporidia by albendazole continues for at least 4 weeks even if the administration was terminated.

1-6: Prevention Test Using Albendazole (4)

A preliminary test was conducted using two administration methods including different administration amounts of albendazole per one operation and different administration intervals. The preliminary test was performed according to the following procedure:

Test cage: 5 m×5 m×5 m

Test number: Live 1000 fishes (each initial body weight: 7 g)

Administration method: oral administration (feed together with spreading agent)

Test period: 6 months

Drug used: albendazole (compound represented by the above-described formula (3))

Administration Amount:

Test group 1: 20 mg/kg Bw (20 mg per kg of fish body weight)

Test group 2: 40 mg/kg Bw (40 mg per kg of fish body weight)

Administration Interval:

Test group 1: 6 times/week (administered for 16 weeks)

Test group 2: 2 times/2 week (administered for 16 weeks)

A sampling test was carried out according to the same procedure as in the above-described 1-5. The results of the sampling test are shown in Table 7 below.

TABLE 7

|  | At administration start time | 8 Weeks | 16 Weeks | 24 Weeks |
| --- | --- | --- | --- | --- |
| Control | 0/20 | 12/60 | 16/70 | 13/50 |
| Test group 1 | 0/20 | 0/50*** | 0/70**** | 16/50 |
| Test group 2 | 0/20 | 0/50*** | 0/70**** | 1/50**** |

***$p < 0.001$
****$p < 0.0001$

Regarding the administration amount of albendazole per each operation and the administration interval, the effect of preventing infection of the beko disease did not continue until 8 weeks after termination of administration of albendazole in the test group 1 which is the same as in the above-described 1-1. On the other hand, significant suppression of generation of the beko cyst was confirmed even at 8 weeks after the termination of administration of albendazole (24 weeks after the start of administration) in the test group 2. The beko cyst confirmed in the test group 2 was old and hardened, thus, it is deemed that the beko syst was not newly generated after the administration of albendazole. These results suggest that resistance to reinjection of the beko disease was obtained in the test group 2 by performing administration of albendazole according to the administration method different from that in the test group 1.

1-7: Prevention Test Using Albendazole (5)

A prevention test against the beko disease by administering albendazole was carried out using "Kanpachi" instead of "Mojako".

A preliminary test was performed according to the following procedure:

Test cage: 5 m×5 m×5 m

Test number: Live 1000 fishes (each initial body weight: 50 g)

Administration method: oral administration (feed together with spreading agent)

Test period: 8 weeks

Drug used: albendazole (compound represented by the above-described formula (3))

Administration amount: 40 mg/kg Bw (40 mg per kg of fish body weight)

Administration interval: 6 times/week

Sampling test procedure: same as in the above-described 1-1

Table 8 below shows the results of the sampling test.

TABLE 8

|  | At administration start time | 8 Weeks |
| --- | --- | --- |
| Control | 1/20 | 10/50 |
| Albendazole group | 1/20 | 1/50** |

**$p < 0.01$

It was confirmed that administration of albendazole significantly suppressed generation of the beko cyst, also in "Kanpachi".

1-8: Prevention Test Using Albendazole (6)

A Prevention test of the beko disease in "Kanpachi" was carried out using triclabendazole. The preliminary test was performed according to the following procedure:

Test cage: 5 m×5 m×5 m

Test number: Live 1000 fishes (each initial body weight: 50 g)

Administration method: oral administration (feed together with spreading agent)

Test period: 8 weeks

Drug used: triclabendazole (compound represented by the above-described formula (10))

Administration amount: 40 mg/kg Bw (40 mg per kg of fish body weight)

Administration interval: 6 times/week

Sampling test procedure: same as in the above-described 1-1

The results of the sampling test are shown in Table 9 below.

TABLE 9

|  | At administration start time | 8 Weeks |
| --- | --- | --- |
| Control | 0/20 | 12/60 |
| Triclabendazole group | 0/20 | 0/50*** |

***$p < 0.001$

It was confirmed that administration of triclabendazole significantly suppressed generation of the beko cyst.

1-9. Prevention Test Using Albendazole (7)

Some microsporidia in humans and animals are susceptible to benzimidazole medicines, and benzimidazole medicines are used as the first-line drugs for these microsporidia. As the action mechanism, it acts on glutamic acid (E) based on the 198th codon for a β-tubulin and inhibits its protein production. The amino acid by the 198th codon of some microsporidia to which benzimidazole is not effective, is that other than glutamic acid. Therefore, it is theoretically predicted that the potential of the benzimidazole medicine as the drug for controlling or preventing microsporidia is high when a β-tubulin gene of a microsporidian, as a pathogen in a fish or a seafood, has a high homology to a β-tubulin gene of a microsporidian having susceptibility to benzimidazole medicines and when the 198th codon is glutamic acid. Then, the β-tubulin genes were isolated from a microsporidian infectious to various fishes or seafoods. Each gene thus isolated was amplified by PCR and its sequencing was performed. Then, its amino acid sequence was confirmed. The results are shown in Table 10 below. The amino acid sequences of a β-tubulin of human and rabbit-derived microsporidia are cited from Franzen C, Salzberger B Analysis of the beta-tubulin gene from Vittaforma corneae suggests benzimidazole resistance. Antimicrob Agents Chemother. 2008 February; 52 (2): 790-3.

TABLE 10

| Name of microsporidia | Origin | Susceptibility to benzimidazole | β-tubulin amino acid sequence |
|---|---|---|---|
| V. corneae | human | NO | 160   165                                                  198<br>PDRML ATFSVVPSPKVSDTVVEPYNATLSIHQLVENAD Q<br>                                                        246<br>TFCIDNDALYDICHKTLKMKSPGYDQLNHLVSLVMSGVTTCLRFPGQ L |
| E. cunicli | rabbit | YES | PDRMI CTFSVVPSPKVSDTVVEPYNATLSIHQLVENAD E<br>TFCIDNEALYDICFRTLKLNNPGYGDLNHLVSLVMSGVTTCLRFPGQ L |
| Beko disease pathogenic microsporidian | "Buri" | YES | PDRMM CTFSVVPSPKVSDTVVEPYNATLSIHQLVENAD E<br>TFCIDNEALYDICFRSLKLTNPGYGDLNHLVSLVMSGVTTCLRFPGQ L |
| Beko disease pathogenic microsporidian | "Kanpachi" | YES | PDRMM CTFSVVPSPKVSDTVVEPYNATLSIHQLVENAD E<br>TFCIDNEALYDICFRSLKLTNPGYGDLNHLVSLVMSGVTTCLRFPGQ L |
| Beko disease pathogenic microsporidian | "Kuromaguro" | ? | PDRMM CTFSVVPSPKVSDTVVEPYNATLSIHQLVENAD E<br>TFCIDNEALYDICFRSLKLTNPGYSDLNHLVSLVMSGVTTCLRFPGQ L |
| Beko disease pathogenic microsporidian | "Madai" | ? | PDRMM CTFSVVPSPKVSDTVVEPYNATLSIHQLVENAD E<br>TFCIDNEALYDICFRSLKLTNPGYGDLNHLVSLVMSGVTTCLRFPGQ L |
| Beko disease pathogenic microsporidian | "Hoshigarei" | ? | PDRMM CTFSVVPSPKVSDTVVEPYNATLSIHQLVENAD E<br>TFCIDNEALYDICFRSLKLTNPGYGDLNHLVSLVMSGVTTCLRFPGQ L |

The homology was very high between an amino acid sequence of a β-tubulin of rabbit-derived microsporidian showing susceptibility to benzimidazole medicines; and the β-tubulin amino acid sequences derived from "Buri", "Kanpachi", "Kuromaguro", "Madai" and "Hoshigarei". Further, the 198th codons of the β-tubulin genes of microsporidia derived from these fishes were all glutaric acid (E). These test results suggest a possibility that microsporidia derived from "Madai", "Hoshigarei" and "Kuromaguro" have susceptibility to benzimidazole.

Example 2: Treatment Test 2-1: Test by Treating "Mojako" Infected with Beko Disease Using Albendazole A treatment test was carried out according to the following procedure.

Test cage: 5 m×5 m×5 m

Test number: Live 1000 fishes (test samples showing apparent infection with beko disease according to visual test at the time of vaccine inoculation were selected and tested)

Administration method: oral administration (feed together with spreading agent)

Test period: 2 months

Drug used: albendazole (compound represented by the above-described formula (3))

Administration amount: 50 mg/kg Bw (50 mg per kg of fish body weight)

Administration interval: 6 times/week

Test Method

Samples of "Mojako" showing irregularities on the body surface with certainty of beko infection in visual test at the time of vaccine inoculation were selected and divided randomly into the control group and the test group. They were taken out 0 day, 10 days and 21 days after the start of administration and each fish was cut into three pieces and it was tested whether the beko cyst was found in the pieces and, when the beko cyst was observed with naked eye, it was judged as positive and the test results were accumulated.

Treatment Test Results

The results are shown in Table 11.

TABLE 11

| | | Number of samples | Number of positive fishes | Infection rate |
|---|---|---|---|---|
| Albendazole group | At administration start time | 10 | 10 | 100% |
| | 10 Days | 10 | 6 | 60% |
| | 21 Days | 63 | 28 | 44.4%** |
| Control group | At administration start time | 10 | 10 | 100% |
| | 10 Days | 10 | 6 | 60% |
| | 21 Days | 82 | 54 | 65.9% |

**$p < 0.01$

1) Regarding Beko Disease Cyst Infection Rate

The fishes recognized to have beko disease cysts according to appearance were selected and subjected to administration tests, then, the numbers of positive samples having beko cysts were accumulated and the results thereof are shown below. Until 10 days after the administration, there was no difference in the infection rate, however, in the results after the termination of administration for 21 days, positive was recognized in 28 out of 63 (44.4%) in the test group, while in 54 out of 82 (65.85%) in the control group. As a result, a significant difference with a risk ratio of less than 1% was recognized.

The invention claimed is:

1. A method for treating or preventing a *Microsporidium seriolae* infection in a fish of the genus *Seriola*, comprising a step of orally administering to a fish of the genus *Seriola* a composition comprising, as an active ingredient, one or more compounds selected from the group consisting of compounds represented by the following chemical formulae (1), (3), (6) and (10), or pharmaceutically acceptable salts thereof,

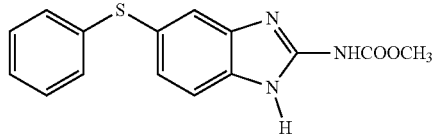
(1)

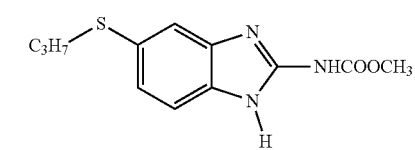
(3)

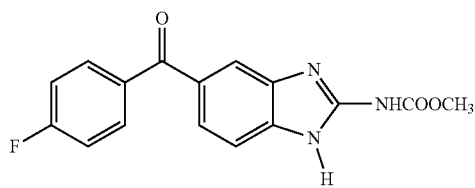
(6)

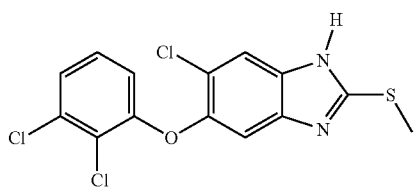
(10)

wherein the composition (i) prevents *Microsporidium seriolae* infection in the muscle or organs of the fish, and/or (ii) suppresses the growth of *Microsporidium seriolae* in the muscle or organs of the fish, and/or (iii) has an activity for eliminating *Microsporidium seriolae* from the body of the fish.

2. The method according to claim 1, wherein the composition is orally administered in a single dose or multiple doses at intervals of not less than 1 day and not more than 180 days so that a dose of the active ingredient is 0.1 mg/kg to 100 mg/kg.

3. The method according to claim 1, wherein the composition is orally administered in a single dose or multiple doses at intervals of not less than 6 hours and not more than 180 days so that a dose of the effective ingredient is 20 mg/kg to 400 mg/kg.

4. The method according to claim 1, wherein the composition is orally administered multiple times at intervals of not less than 3 days and not more than 180 days so that a dose of the active ingredient is 20 mg/kg to 400 mg/kg.

5. The method according to claim 4, wherein the composition is orally administered at intervals of not less than 5 days and not more than 21 days.

6. The method according to claim 4, wherein the multiple oral administrations are carried out as one cycle and the cycle is repeated at intervals of not less than 3 days and not more than 180 days.

* * * * *